United States Patent [19]

Boenko et al.

[11] Patent Number: 5,011,491
[45] Date of Patent: Apr. 30, 1991

[54] SURGICAL FORCEPS

[76] Inventors: Sergei K. Boenko, Shakhtostroitelei, 20, kv. 52; Alexandr Y. Shvartsman, Artema, 159, kv. 94, both of Donetsk, U.S.S.R.

[21] Appl. No.: 480,736

[22] Filed: Feb. 16, 1990

[30] Foreign Application Priority Data

Feb. 27, 1989 [SU] U.S.S.R. ............... 4651605

[51] Int. Cl.⁵ ............................................. A61B 17/28
[52] U.S. Cl. ........................................ 606/207; 81/418
[58] Field of Search ................... 606/205–207, 606/157, 210; 81/417, 418, 421, 424.5, 426, 426.5; 433/4, 159, 160

[56] References Cited

U.S. PATENT DOCUMENTS

| | | | |
|---|---|---|---|
| 2,642,871 | 6/1953 | Thuerig | 606/207 |
| 3,209,753 | 10/1965 | Hawkins et al. | 606/207 |
| 3,608,554 | 9/1971 | McGuiness et al. | 606/207 |
| 3,842,696 | 10/1976 | Wanye | 81/424.5 |
| 4,024,870 | 5/1977 | Sandel | 81/424.5 |
| 4,386,461 | 6/1983 | Plummer | 81/424.5 |
| 4,667,671 | 5/1987 | Danzig | 606/157 |

OTHER PUBLICATIONS

Orthopli Catalog, 1978.

Primary Examiner—C. Fred Rosenbaum
Assistant Examiner—William W. Lewis
Attorney, Agent, or Firm—Burgess, Ryan & Wayne

[57] ABSTRACT

A surgical forceps comprises two blades, each of which having a handle with a circular rest for fingers and a lock, and a jaw, incorporating a shank made integral with the handle, and a plate provided at the shank vacant end. A rectangular projection is provided on the flat surface of one of the blades, arranged along the plate longitudinal axis, and a slot with a concave bottom whose longitudinal axis is square with the longitudinal axis of the plate. A slit is provided in the plate of the other blade, arranged along the longitudinal axis of the plate, while its flat surface has an oval projection whose longitudinal axis is square with the longitudinal axis of the plate. The handles of the blades are so hinge-joined together that the afore-mentioned flat surfaces of the plates face towards each other.

1 Claim, 2 Drawing Sheets 5,011,491

SURGICAL FORCEPS

FIELD OF THE INVENTION

The present invention relates generally to medical instruments and more specifically to surgical forceps.

The present invention is successfully applicable in carrying out surgical vocal rehabilitation in patients who have sustained total laryngectomy for carcinoma and in whom sticking together of tissues is performed when establishing a tracheoesophageal opening with a lip made of a cartilaginous semiring.

BACKGROUND OF THE INVENTION

Surgical vocal rehabilitation in patients sustained total laryngectomy has been developed for the recent 20 to 25 years. However, such surgery is rather traumatic and long-duration, and fails to prevent aspiration of saliva and alimentary mass into the tracheobronchial tree.

One state-of-the-art surgical forceps (FR, A, 2,074,063) is known to comprise a first blade having a handle that features a first and a second end, a circular rest for a finger located at said first end of said handle, a lock situated at said first end of said handle, and a jaw having a serrated surface featuring projections and recesses; a second blade having a handle that features a first and a second end, a circular rest for a finger located at said first end of said handle, a lock situated at said first end of said handle and adapted to interact with said lock of said first blade, while said second ends of said handles of said first and second blades hinged-joined together, and a jaw having a serrated surface featuring projections and recesses, wherein said projections and recesses are adapted to interact with said respective recesses and projections of said serrated surface of said jaw of said first blade.

However, when said surgical forceps is employed for pressing irregular-surface tissues the serrated surfaces of the jaws fail to provide uniform fixing of tissues between the jaws, which affects adversely reliability of fixing the tissues.

Besides, in said surgical forceps the serrated surfaces of the jaws fail to 'take account' of an irregular surface of tissues when pressing the latter, which results in increased traumatism of the protruding areas of the tissues.

SUMMARY OF THE INVENTION

It is an object of the present invention to provide a surgical forceps capable of adding to the reliability of tissue fixing.

It is another object of the present invention to reduce the degree of traumatism inflicted upon the tissues being operated.

The objects of the invention are accomplished due to the fact that a surgical forceps incorporates a first blade provided with a handle which has a first end and a second end, a circular rest for a finger, said rest being located at said first end of said handle, a lock situated at said first end of said handle, and a jaw, comprising a shank which has a first end and a second end, said first end of said shank being connected to said second end of said handle, a rectangular plate having a longitudinal axis, a first end face and a second end face, a flat surface, a rectangular slit nearby said first end face, said slit being arranged along said longitudinal axis of said rectangular plate, and a projection having a rectangular base, a convex surface, a height and a longitudinal axis, said projection being so arranged close to said second end face that its said longitudinal axis is square with the longitudinal axis of said rectangular plate, while said second end face of said rectangular plate is connected to said second end of said shank; a second blade, comprising a handle provided with a handle which has a first end and a second end, a circular rest for a finger, said rest being located at said first end of said handle, a lock situated at said first end of said handle and adapted to interact with said lock of said first blade, said second ends of said handles of said first and second blades hinge-joined together, and a jaw, comprising a shank which has a first end and a second end, said first end of said shank being connected to said second end of said handle, a rectangular plate having a longitudinal axis, a first end face and a second end face, and a flat surface that faces towards said flat surface of said rectangular plate of said jaw of said first blade, a rectangular projection having such geometric dimensions that are smaller than those of said rectangular slit of said rectangular plate of said jaw of said first blade, said projection being located on said flat surface nearby said first end face along said longitudinal axis, and a rectangular slot congruent with said projection of said rectangular plate of said jaw of said first blade, said slot having a concave bottom and whose depth is smaller than said height of said projection congruent therewith, which slot is situated close to said first end face so that its said longitudinal axis is square with said longitudinal axis of said rectangular plate.

The present invention provides for a uniform fixing of tissues, thus rendering such fixing more reliable.

In addition, the present invention 'take account' of the configuration of the surface of tissues when pressing the latter, which reduces the degree of traumatism inflicted on the tissues.

BRIEF DESCRIPTION OF THE DRAWINGS

Further objects and advantages of the present invention will become evident hereinbelow upon consideration of a specific exemplary embodiment thereof with reference to the accompanying drawings, wherein.

Figure 1:
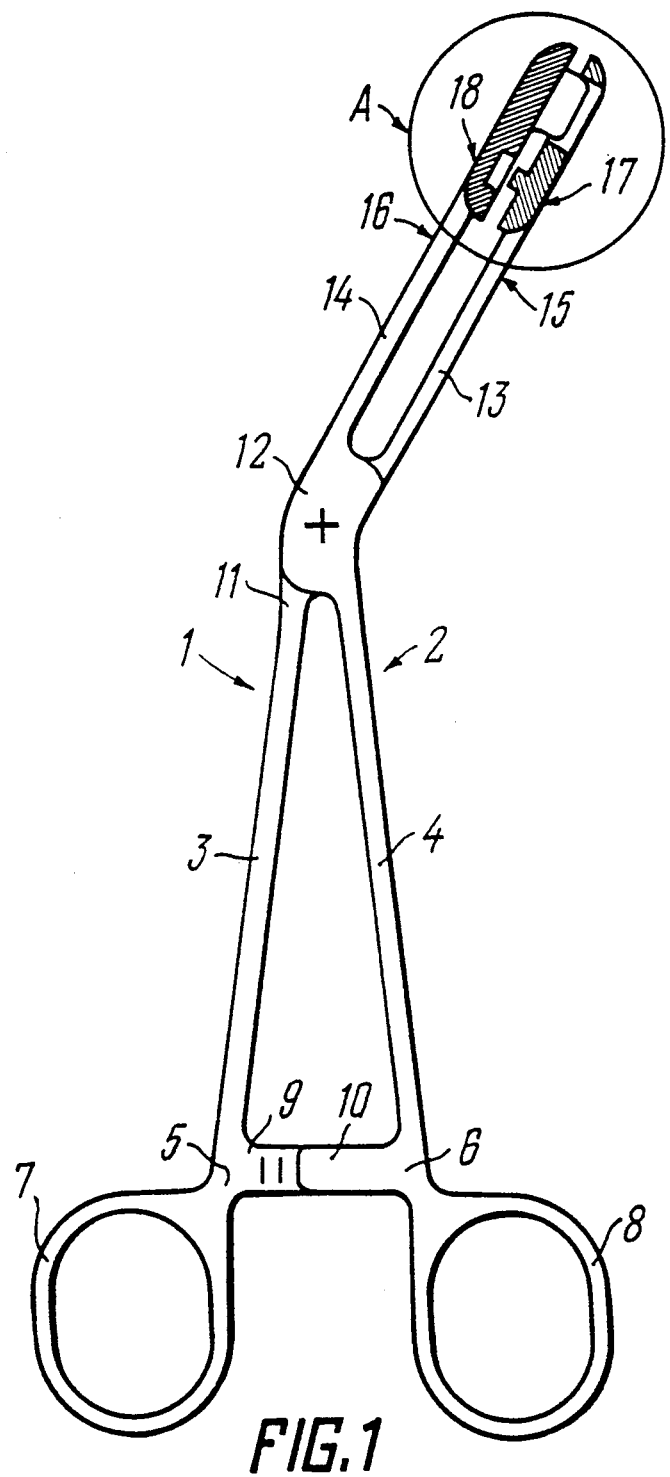
FIG. 1 is a general fragmentarily sectional view of a surgical forceps, according to the invention.
Figure 2:
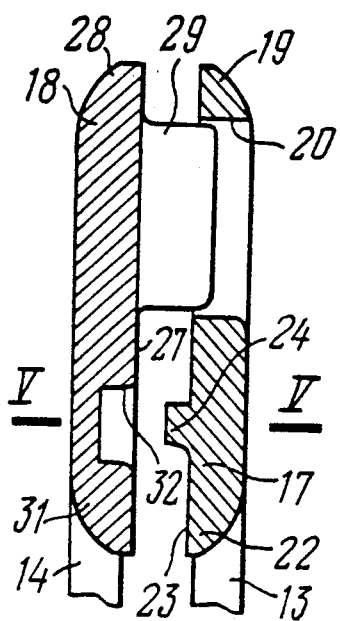
FIG. 2 is a scaled-up longitudinal sectional view of a unit A in FIG. 1.
Figure 3:
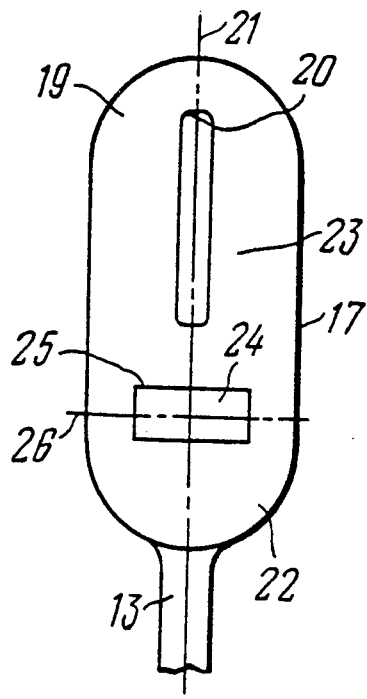
FIG. 3 is a general view of a plate with a slit and a projection as shown in FIG. 1, according to the invention.
Figure 4:
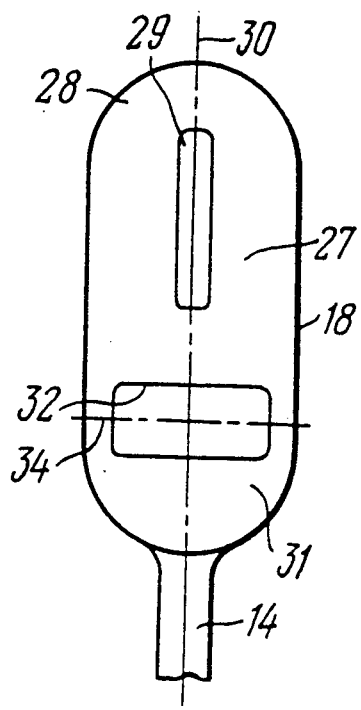
FIG. 4 is a general view of a plate with a projection and a slot as shown in FIG. 1, according to the invention.
Figure 5:
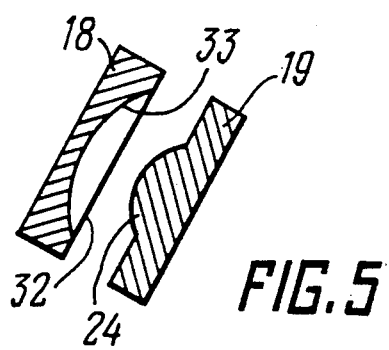
FIG. 5 is a section taken along the line V—V in FIG. 2.

The surgical forceps comprises two blades 1, 2 (FIG. 1), each of which has respective handles 3 and 4. One ends 5, 6 of the respective handles 3, 4 are provided with circular rests 7, 8 for fingers, and locks 9, 10. Other ends 11, 12 of the respective handles 3, 4 carry respective shanks 13, 14 of respective jaws 15, 16, said shanks being made integral with said handles 3, 4. The vacant ends of the shanks 13, 14 are provided with rectangular plates 17, 18 (FIGS. 1, 2) shown with arcuate ends. A rectangular slit 20 (FIGS. 2, 3) is made in the plate 17 close to its vacant end face 19, said slit being arranged coaxially with a longitudinal axis 21 of the plate 17, whereas an oval projection 24 (FIGS. 2, 5) is provided on a flat surface 23 of the plate 17 close to its other end face 22, said projection having a rectangular base 25 and whose longitudinal axis is square with the axis 21. A rectangular projection 29 is provided on a flat surface 27 (FIGS. 2, 4) of the plate 18 close to its vacant end face 28, said projection being arranged coaxially with a longitudinal axis 30 of the plate 18. A slot 32 having a concave bottom 33 is provided nearby another end face 31 of the plate 18, a longitudinal axis 34 of said slot being square with the axis 30. The ends 11, 12 (FIG. 1) of the respective handles 3, 4 are hinge-joined together in such a manner that the flat surfaces 23 and 27 (FIG. 2) of the respective plates 17 and 18 are free to interact with each other. At the instant of such interaction of the flat surfaces 23 and 27 of the respective plates 17 and 18 the projection 24 on the flat surface 23 engages the slot 32 on the flat surface 27, while the projection 29 on the flat surface 27 engages the slit 20 on the flat surface 23 at an air gap.

Given below is an exemplary application of the proposed surgical forceps in surgery for vocal rehabilitation following total laryngectomy.

Once the dorsal tracheal wall has been preliminarily fixed to the ventral esophageal wall presmeared with a medical adhesive round its bypass opening, and to the concave inner surface of a cartilaginous semiring, the surgical forceps of the present invention is applied as follows.

The plate 18 with the projection 29 on the blade 2 is inserted into the esophageal cavity and is so arranged that the projection 29 should enter the bypass opening. As a result, the projection formed by the ventral esophageal wall and the cartilaginous semiring occurs in level with the slot 32. Then the blades 1 and 2 are brought together until the plate 18 interacts with the dorsal tracheal wall but so that the tissues pressed between the surfaces 23 and 27 of the respective plates 17 and 18 neither be crushed nor bruised, whereupon the locks 9, 10 are closed. As a result, the projection 29 engages the slit 20, while the projection 24 causes the projection formed by the ventral esophageal wall and the cartilaginous semiring with the dorsal tracheal wall to enter the slot 32.

The present invention provides for reliable fixing of tissues during their being stuck together, which results in the establishment of an efficient bypass opening and a projection thereabove.

What is claimed is:

1. A surgical forceps, comprising:
a first blade, incorporating:
a handle having a first end and a second end;
a circular rest for a finger, said rest being located at said first end of said handle;
a lock situated at said first end of said handle;
a jaw, comprising:
a shank having a first end and a second end, said first end being connected to said second end of said handle;
a rectangular plate having a longitudinal axis, a first end face and a second end face, a flat surface, a rectangular slit situated close to said first end face and arranged along said longitudinal axis of said rectangular plate, and a projection having a rectangular base, a convex surface, a height and a longitudinal axis, said projection being so arranged close to said second face that the longitudinal axis of said projection is square with the longitudinal axis of said rectangular plate, said second end face of said rectangular plate is connected to said second end of said shank;
a second blade, comprising:
a handle having a first end and a second end;
a circular rest for a finger, said rest being located at said first end of said handle;
a lock situated at said first end of said handle and adapted to interact with said lock of said first blade;
said second ends of said handles of said first and second blades hingedly joined together;
a jaw, comprising:
a shank having a first end and a second end, said first end being connected to said second end of said handle;
a rectangular plate having a longitudinal axis, a first end face and a second end face, and a flat surface that faces towards said flat surface of said rectangular plate of said jaw of said first blade, a rectangular projection having such geometric dimensions that are smaller than those of said rectangular slit of said rectangular plate of said jaw of said first blade, said projection being located on said flat surface nearby said first end face along said longitudinal axis, and a rectangular slot having a longitudinal axis and being congruent with said projection of said rectangular plate of said jaw of said first blade, said slot having a concave bottom and whose depth is smaller than said height of said projection congruent therewith, which slot is situated close to said first end face so that the longitudinal axis of the slot is square with said longitudinal axis of said rectangular plate.

* * * * *